United States Patent [19]

Gardineer et al.

[11] 4,399,704
[45] Aug. 23, 1983

[54] ULTRASOUND SCANNER HAVING COMPOUND TRANSCEIVER FOR MULTIPLE OPTIMAL FOCUS

[75] Inventors: Bayard Gardineer, Skillman, N.J.;
Reuben S. Mezrich, Miami, Fla.;
George W. Leber, Delran, N.J.

[73] Assignee: Technicare Corporation, Solon, Ohio

[21] Appl. No.: 270,049

[22] Filed: Jun. 3, 1981

[51] Int. Cl.³ .......................................... G01N 29/00
[52] U.S. Cl. .................................... 73/642; 310/335
[58] Field of Search ................ 73/642, 606, 607, 620,
73/624, 625, 632, 633; 310/335, 334, 336;
367/150, 7, 103

[56] References Cited

U.S. PATENT DOCUMENTS

| | | | |
|---|---|---|---|
| 4,097,835 | 6/1978 | Green | 73/642 |
| 4,131,021 | 12/1978 | Mezrich et al. | 73/606 |
| 4,131,022 | 12/1978 | Mezrich | 73/606 |
| 4,271,706 | 6/1981 | Ledley | 73/620 |

*Primary Examiner*—Stephen A. Kreitman
*Attorney, Agent, or Firm*—W. Brinton Yorks, Jr.; Audley A. Ciamporcero

[57] ABSTRACT

A circular ultrasound transducer is divided into separate semi-circular transducer elements. Each element is separately operable, and each is aligned with similarly configured lens segments having different focal zones.

8 Claims, 10 Drawing Figures

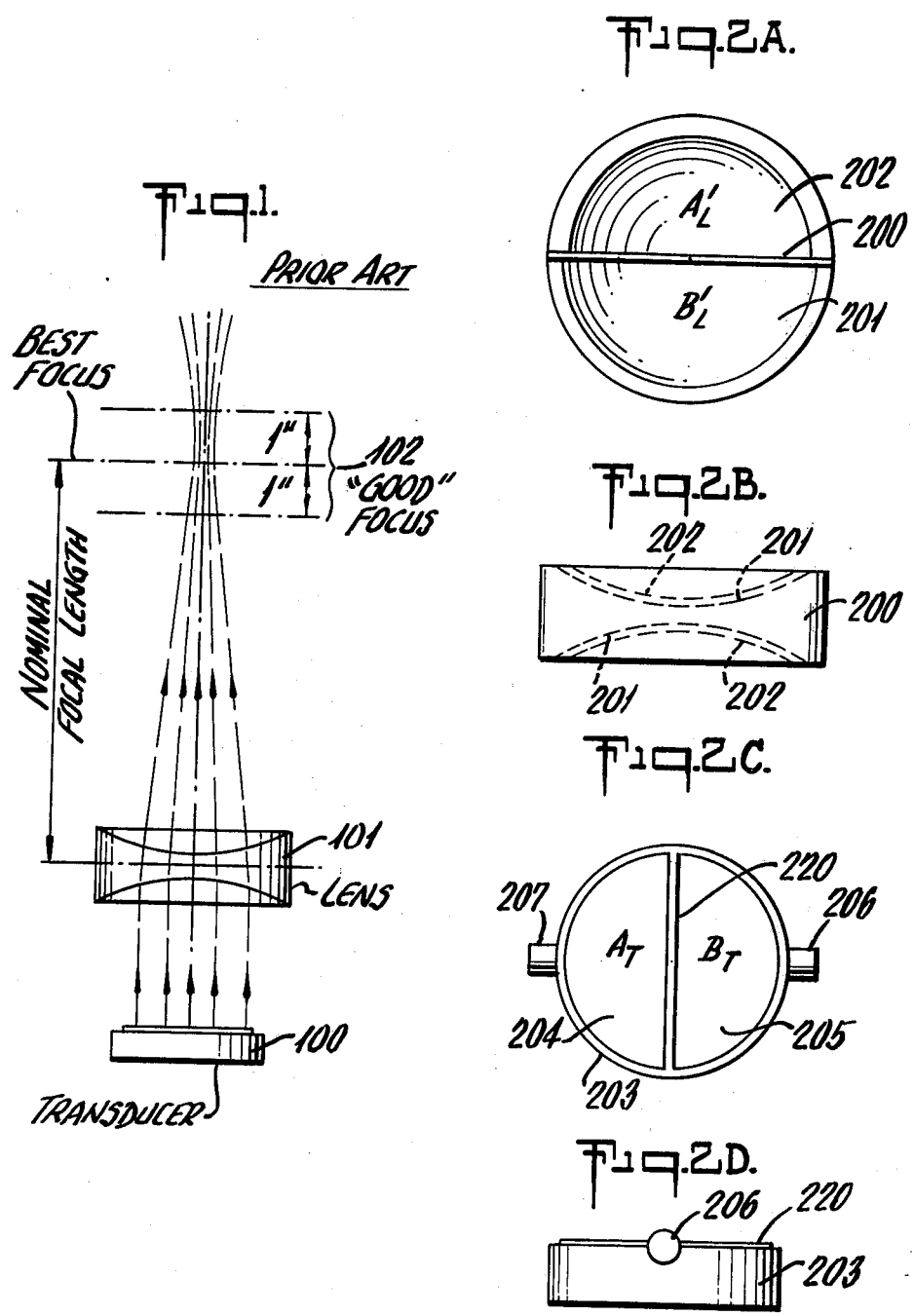

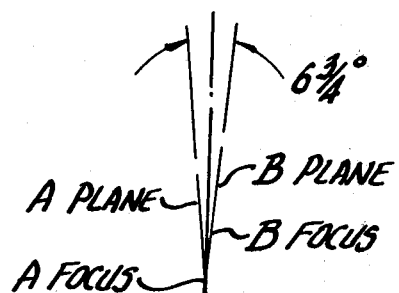
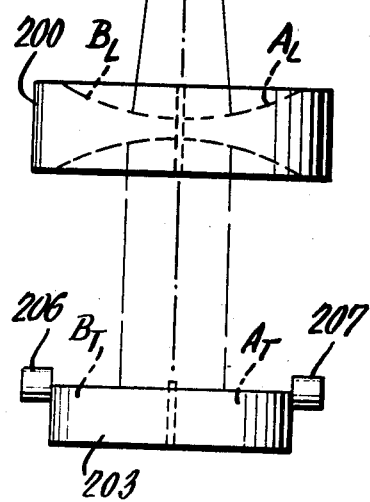
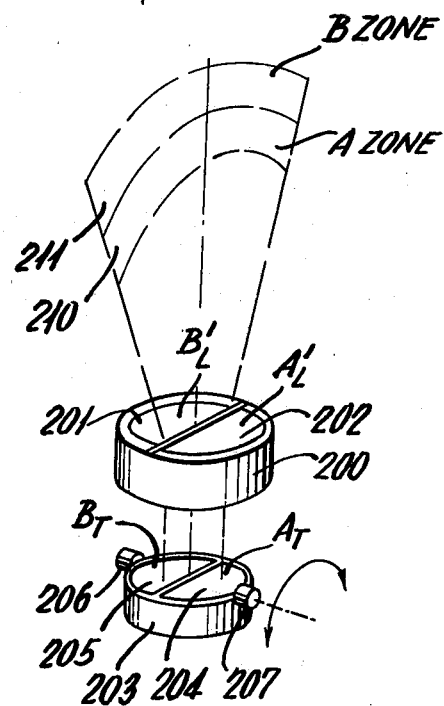
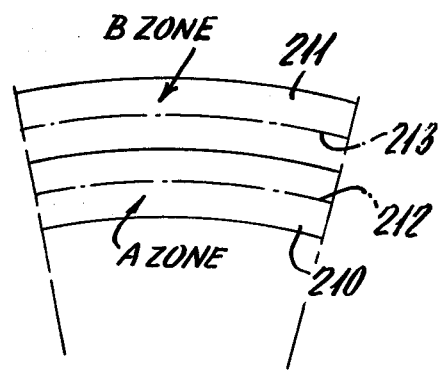

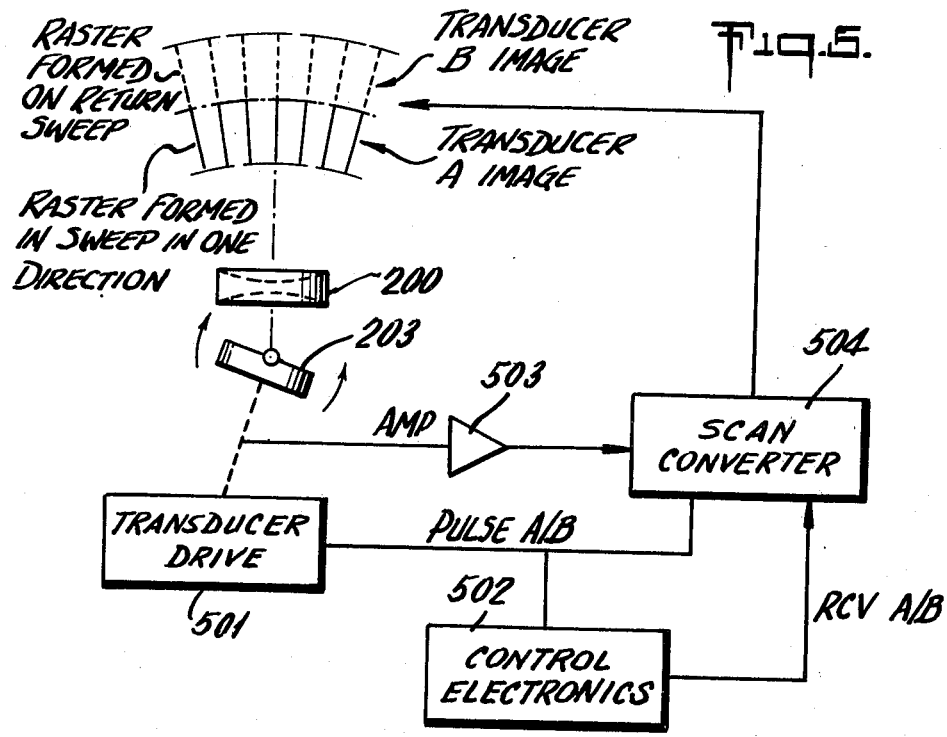
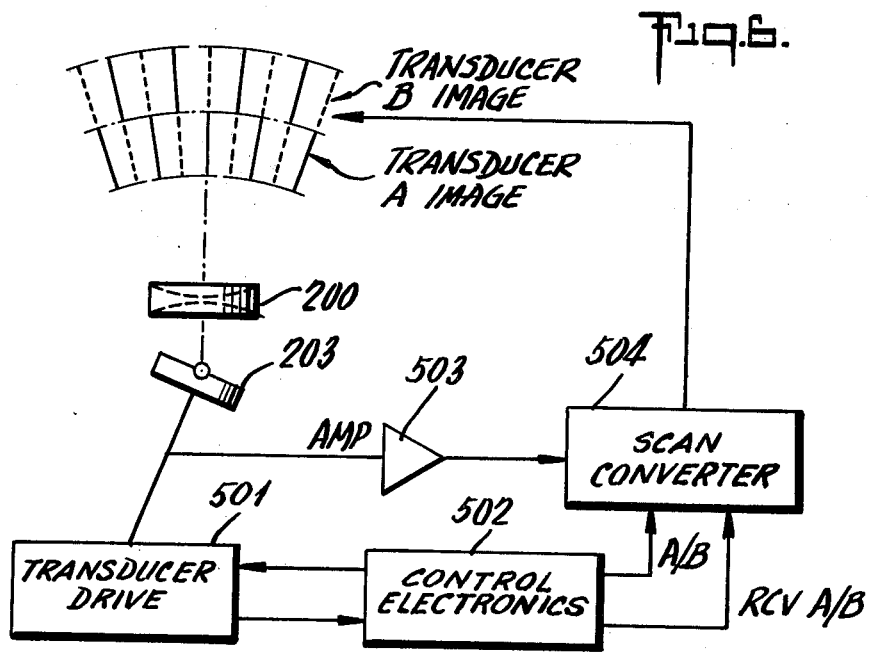

ULTRASOUND SCANNER HAVING COMPOUND TRANSCEIVER FOR MULTIPLE OPTIMAL FOCUS

FIELD OF THE INVENTION

This invention relates to ultrasound imaging systems, and in particular to methods and apparatus for improving the field of focus and resolution in such systems.

BACKGROUND OF THE INVENTION AND PRIOR ART

A perennial problem in the design of diagnostic ultrasound systems is that of realizing relatively optimal spacial resolution over the entire depth range of the image plane. Thus, while individual approaches to design of ultrasound imaging systems dictate different compromises in design, operation, or ultimate image quality, the underlying difficulty is never far from the surface.

One well known class of ultrasound imaging system is that which utilizes a transducer element and an associated acoustic lens for generation of sonic transmissions, and receipt of sonic echoes, based upon which the image is constructed. See, for example, U.S. Pat. Nos. 4,131,021 and 4,131,022 to Mezrich et al., and an extensive series of improvement patents. In one version of system in this class, which has found greatest commercial favor, the transducer and lens both are circular in configuration and spaced apart, the lens is stationary, and the transducer is oscillated or "nodded" through predetermined arc. Transmission and receipt of echo pulses occurs at predetermined increments of the arc, and the compbsite of the individual echoes is a B-scan.

In accordance with the transducer-lens approach to ultrasound design, the convergence of the sonic beam results in a zone of focus at which the beam is narrowest, and on both sides of which it gradually diverges. The outer points of the "good focus" zone are of course subjectively defined, depending upon the nature of the imaging being conducted, and the corresponding tolerance of relatively poorer spacial resolution at the top and bottom of the image field. Parenthetically, it is to be noted that the same condition obtains in those systems wherein a lenslike focusing element is attached directly to the front of a flat transducer element, or wherein the transducer itself has a curved or shaped beam focusing surface.

One prior art approach to expansion of the high resolution segment of the image field has been to divide the planar transducer into a multiple ring concentric annular array, each ring of which, in association with the lens, has a different optimal focal characteristic. In the aggregate, there results an extended field of well focused ultrasound energy. Annular array transducers, however, are quite difficult to design and fabricate, and are inherently structurally complex; they also require complex and expensive support electronics, and, as of the current state of the art, are notoriously unreliable. Moreover, increases in the multiplicity of annular ring elements result in corresponding increases in supporting cable connections and the like. This sheer physical bulk mitigates against elegant and reliable transducer oscillation mechanisms, connections, and designs. Finally, empirical design considerations for annular array systems often entail compromises which substantially reduce the high resolution field depth capability from that which is theoretically available.

It is accordingly a primary object of the present invention to provide ultrasound scanning systems, and especially those of the transducer and lens type, which present extended zones of acceptable focus and hence of satisfactory spatial resolution, while avoiding annular transducer arrays and the difficulties inherent in those schemes.

SUMMARY OF THE INVENTION

The principles of the present invention derive from the premise that a sonic lens may be divided into separate semicircular portions, each having a different focal characteristic. Each therefore defines a different optimal focus zone, and when properly configured, they together define a single, elongated zone of relatively optimal focus. Such a lens operates in conjunction with a transducer which is similarly divided into a pair of respectively aligned semicircular planar transducer elements. Superposition of the pulse-echo events at the respective transducer segments produces the composite image.

In a preferred embodiment, a planar transducer is composed of a pair of adjacent, back to back semicircular or "D" shaped transducer elements, each being independently operable to transmit and receive sonic energy. The transducer unit is mounted to pivot about an axis perpendicular to the plane dividing the two transducer elements. The transducer unit is spaced from a fixed lens which also is of a back to back, "double-D" configuration, the "D's" of the transducer being aligned with those of the lens. The lens "D's" are respectively designed to have substantially contiguous zones of high convergence. As the transducer is nodded back and forth through its arc, the two transducer elements are suitably conditioned to transmit and receive sonic energy pulses, each through its respectively associated lens half, and the overall image field is assembled based on echo information from both transducer halves.

DESCRIPTION OF THE DRAWINGS

FIG. 1 shows a schematic representation of a prior art transducer/lens ultrasound imaging system.

FIGS. 2A and 2B show respective top and side views of a lens in accordance with the principles of the present invention, and FIGS. 2C and 2D show respective top and side views of a compound transducer in accordance with the principles of the present invention.

FIGS. 3, 4A, and 4B show various views of an illustrative embodiment of the principles of the present invention.

FIGS. 5 and 6 show alternative forms of imaging systems employing the principles of the present invention.

BEST MODE FOR CARRYING OUT THE INVENTION

Referring first to FIG. 1, there is shown a schematic side view of a conventional ultrasound imaging system employing a transducer and lens. In particular, the transducer 100 is aligned with and spaced a predetermined distance from a lens 101, such that sonic energy from the transducer 100 passes through and is focused by the lens 101, achieving optimal convergence, and hence focus, a nominal focal length (associated with the physical structure and character of the lens 101) away from the lens 101. As will be noted, the sonic energy converges between the lens and the "best focus" point, whereupon, due to scattering by the tissue and the like it begins to diverge. Hence, depending upon the desired spatial resolution of the system, a well focused zone 102 may be subjectively defined, extending predetermined distances on either side of the "best focus" point. For example, in a prior art system of the sort set forth in FIG. 1, which achieves spatial resolution of approximately 2 millimeters, is characterized by a 3 inch diameter transducer 100 excited in the 3.0 megahertz range, resulting in a well focused zone 102 of 2 inches depth, approximately half on either side of the "best focus" line.

Clearly, many everyday applications dictate investigation of tissue zones substantially greater than 2 inches in depth and many of these are not situations where trained and sophisticated sonographers have the time and ability to manipulate the instruments in real time freely to investigate the entire volume of tissue in question. For example, high volume breast scanning applications involve a single, rapid accumulation of substantially parallel transverse B-scans, with each scan covering the entire depth of tissue. A physician or diagnostician typically will review these images later, when the patient is unavailable for more detailed scans. Clearly, in such applications, it is necessary to have a system which employs full field depth for each single scan pass.

In accordance with the principles of the present invention both the transducer and the lens of the system transceiver are to be divided into separate, functionally independent back to back semicircular halves, (i.e. each in the shape of a "D"). In particular, FIGS. 2A and 2B show respective top and side views of such a lens element 200, wherein one side 202, designated side "$A'_L$" has a first predetermined lens curvature, and the other side 201 designated side "$B'_L$" has a different predetermined lens curvature. Hence, sonic energy passing through side "$A'_L$" 202 will be deflected by an amount dictated by the thickness of the lens material through which it passes on that side (and therefore be characterized by one nominal focal length). Sonic energy passing through the other side "$B'_L$" 201 shall be deflected based on passage through different thicknesses of lens material (and therefore be characterized by a different nominal focal length).

FIGS. 2C and 2D show transducer apparatus, operable in conjunction with the lens apparatus of FIGS. 2A and 2B, in accordance with the principles of the present invention. Thus, a frame member or bracket 203 carries a pair of separate, coplanar semicircular functionally independent ("D" shape) transducer elements "$A_T$" 204 and "$B_T$" 205. The transducer unit is mountable at 206 and 207 to pivot about an axis "x—x", where that axis lies in the plane of the two transducers 204 and 205 but orthogonal to the dividing portion 220 of the transducer frame member 203. In a system, the segment "$A_T$" 204 is operatively associated with and physically aligned with section "$A_L$" 202 of the lens, whereas section "$B_T$" 205 of the transducer is operatively associated with, and physically aligned with section "$B_L$" 201 of the lens 200.

Operation of the principles of the present invention may perhaps be best appreciated upon consideration of FIGS. 3, 4A, and 4B, which shown various views of an ultrasound system employing the principles of the present invention. Hence, the "A" sections of transducer and lens will together image a well focused zone "A" 210, whereas their opposite counterparts will together image a well focused zone "B" 211. In a preferred embodiment, the respective focal zones A and B are to be spatially contiguous, thereby producing, when properly processed, an elongated composite focal zone.

These well focused zones are centered at distances shown as respective arcs 212 and 213 in FIG. 4B. In the aggregate, a scan plane of approximately double the single lens depth of focus results. It should be noted that due to the lateral offset of the respective "A" and "B" transceiver halves, the respective zones 210 and 211 are not coplanar. Instead, as shown in the transverse view of FIG. 4A, and "A" and "B" zones are tilted relative to one another at an angle of approximately 6¾ degrees.

It will be appreciated that transducer-lens (i.e. transceiver) designs in accordance with the principles of the present invention allow the designer considerable flexibility in selecting a mode of operation for accumulation of a complete scan plane based on the fixed lens, oscillating transducer rationale. FIGS. 5 and 6 depict schematic system diagrams for alternative approaches. In brief, FIG. 5 depicts a rationale wherein one of the transducer halves 204 or 205 is conditioned to transmit and receive sonic energy during alternate nods or half oscillations of the transducer 203, while the other half is conditioned to transmit and receive sonic energy during complementary alternate nods or half oscillations of the transducer 203. In contrast, in the system depicted in FIG. 6, each half of the transducer is conditioned to generate and receive sonic energy at each alternate periodic angular increment at each half traversal but in a complementary way so that a full raster results.

Said otherwise, the system shown in FIG. 5 operates by pulsing (for example at a rate of 600 microseconds) transducer half "$A_T$" 204 for each increment of the angular transducer sweep in one direction, say the counter-clockwise direction, and by pulsing the other transducer half "$B_T$" 205 at the same intervals during the return, or clockwise sweep. In conventional fashion, the scan converter 504 receives the echo data via amplifier 503, and stores the data for both clockwise and counter-clockwise transducer sweeps. In the aggregate, a full field image raster is assembled in the scan converter 54 at the termination of a complete clockwise-counter-clockwise transducer oscillation cycle.

The drawback of the approach embodied in the FIG. 5 system is chiefly in the lack of interlace, and hence sensitivity to patient motion. A remedy for this difficulty is achieved, at some small cost in system complexity, by the system of FIG. 6. As shown, both transducer halves are excited alternately at all intervals during block clockwise and counter-clockwise transducer sweeps, resulting in a full raster interlace accumulation at the scan converter 504 for each full oscillation cycle of the transducer. Both systems employ transducer drive systems 501, send and receive control electronics 502, scan converters 504, and associated apparatus generally of the type employed in ultrasound imaging systems, the design of which is well within the capability of those of ordinary skill in the art.

The foregoing has set forth preferred and illustrative embodiments of the principles of the present invention, and it is to be understood that numerous alternative embodiments will occur to those of ordinary skill in the art without departure from the spirit or the scope of the principles of the present invention.

We claim:

1. In an ultrasound image system, the improvement comprising:

transducer means of generally circular shape and having at least two sector shaped transducer components, each said component being separately operable to transmit and receive sonic energy for imaging; and means associated with said transducer means having respective sector shaped focusing segments for focusing energy from said respective transducer components into respective different predetermined focal zones.

2. Apparatus as described in claim 1 wherein said means for focusing comprises an acoustic lens divided into sectors respectively associated with said sector shaped components of said transducer means, each said lens sector being characterized by focusing characteristics associated with said different predetermined focal zones.

3. Apparatus as described in claim 2 wherein said transducer means and said acoustic lens each define two semicircular segments as said sectors, wherein each of said mutually operationally independent transducer semi-circular segments is spatially aligned a given distance from a different one of said lens semicircular segments.

4. Apparatus as described in claim 3 and further including means for physically oscillating said transducer means and said acoustic lens relatively to one another while maintaining partial alignment between respectively associated transducer and lens segments, thereby to produce an ultrasound image plane having respective different depth of focus zones produced by said respectively associated segments.

5. Apparatus as described in claim 4 wherein said lens is maintained fixed and said transducer means is oscillated through an arc of predetermined dimension and about an axis orthogonal to a line dividing said semicircular transducer segments.

6. Apparatus as described in claim 5 and further including means for alternately energizing said semi-circular transducer components at predetermined angular intervals through said arc.

7. Apparatus as described in claim 5 and further including means for energizing a first one of said semi-circular transducer segments at predetermined angular intervals through alternate transversals of said arc by said transducer means, and for energizing a second of said intervals during interleaved alternate transversals of said arc by said transducer means.

8. Apparatus as described in claim 2, wherein said different predetermined focal zones are substantially contiguous.

* * * * *